United States Patent
Kamee et al.

(10) Patent No.: US 10,799,102 B2
(45) Date of Patent: Oct. 13, 2020

(54) ILLUMINATION APPARATUS, ENDOSCOPIC SYSTEM, AND COLOR CORRECTION APPARATUS

(71) Applicant: OLYMPUS CORPORATION, Tokyo (JP)

(72) Inventors: Hiroyuki Kamee, Tokyo (JP); Hiromasa Fujita, Tokyo (JP); Masahiro Nishio, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 604 days.

(21) Appl. No.: 15/659,756

(22) Filed: Jul. 26, 2017

(65) Prior Publication Data
US 2017/0319053 A1    Nov. 9, 2017

Related U.S. Application Data

(63) Continuation of application No. PCT/JP2015/000429, filed on Jan. 30, 2015.

(51) Int. Cl.
*A61B 1/06* (2006.01)
*G02B 23/26* (2006.01)
(Continued)

(52) U.S. Cl.
CPC .............. *A61B 1/0661* (2013.01); *A61B 1/06* (2013.01); *G02B 23/2469* (2013.01);
(Continued)

(58) Field of Classification Search
CPC ...... G02B 23/24; G02B 23/26; A61B 1/0661; A61B 1/0638; A61B 1/0646; A61B 1/0653; A61B 1/07; A61B 1/06
See application file for complete search history.

(56) References Cited

U.S. PATENT DOCUMENTS

2013/0018242 A1*  1/2013  Yamaguchi .......... A61B 5/0084
                                                  600/339
2013/0296652 A1*  11/2013  Farr ..................... A61B 1/0676
                                                  600/109
(Continued)

FOREIGN PATENT DOCUMENTS

JP      H10-286235 A      10/1998
JP      2002-122794 A      4/2002
(Continued)

OTHER PUBLICATIONS

International Search Report dated Apr. 21, 2015 issued in PCT/JP2015/000429.
(Continued)

*Primary Examiner* — Matthew J Kasztejna
(74) *Attorney, Agent, or Firm* — Scully, Scott, Murphy & Presser, P.C.

(57) ABSTRACT

An illumination apparatus in an endoscopic system includes a light source unit having lasers with different peak wavelengths, the lasers being divided by peak wavelength into narrow band light source groups, a color imaging unit that detects the illumination color of illumination light, a memory that stores an appropriate illumination color for each narrow band light source group, an output calculator that, for each narrow band light source group, compares the illumination color obtained upon light emission by the lasers belonging to the narrow band light source group with the appropriate illumination color of the narrow band light source group and calculates an appropriate output for each of the lasers belonging to the narrow band light source group, and a light source controller that controls the lasers on the basis of the calculated appropriate output.

13 Claims, 13 Drawing Sheets

(51) Int. Cl.
  *G02B 23/24* (2006.01)
  *A61B 1/04* (2006.01)
(52) U.S. Cl.
  CPC ............... *G02B 23/26* (2013.01); *A61B 1/04* (2013.01); *A61B 1/0638* (2013.01); *A61B 1/0646* (2013.01)

(56) References Cited

U.S. PATENT DOCUMENTS

| | | | | |
|---|---|---|---|---|
| 2014/0055585 | A1* | 2/2014 | Akiyama | G02B 23/2469 348/68 |
| 2014/0187881 | A1* | 7/2014 | Saito | A61B 1/0638 600/323 |
| 2015/0087903 | A1* | 3/2015 | Kuramoto | A61B 1/00059 600/109 |
| 2015/0245002 | A1* | 8/2015 | Kuramoto | A61B 1/00009 348/70 |
| 2015/0335232 | A1* | 11/2015 | Ito | A61B 1/07 362/13 |
| 2016/0331218 | A1* | 11/2016 | Kamee | G02B 23/2461 |

FOREIGN PATENT DOCUMENTS

| | | |
|---|---|---|
| JP | 2005-034166 A | 2/2005 |
| JP | 5467181 B1 | 4/2014 |
| JP | 2014-150932 A | 8/2014 |

OTHER PUBLICATIONS

Chinese Office Action dated Apr. 28, 2018 in Chinese Patent Application No. 201580071644.2.
English translation of International Preliminary Report on Patentability dated Aug. 10, 2017 together with the Written Opinion received in related International Application No. PCT/JP2015/000429.

* cited by examiner

ILLUMINATION APPARATUS, ENDOSCOPIC SYSTEM, AND COLOR CORRECTION APPARATUS

CROSS-REFERENCE TO RELATED APPLICATION

The present application is a Continuing Application based on International Application PCT/JP2015/000429 filed on Jan. 30, 2015, the entire disclosure of which is incorporated herein by reference.

TECHNICAL FIELD

This disclosure relates to an illumination apparatus, an endoscopic system using the illumination apparatus, and a color correction apparatus.

BACKGROUND

With respect to conventionally used light sources, solid-state light sources such as LEDs and lasers offer a variety of advantages, including low power consumption, high connection efficiency, compactness, and high-speed switching. Innovation regarding such solid-state light sources is astounding, and solid-state light sources have been progressively applied to endoscopes as a replacement for conventional light sources. In general, solid-state light sources characteristically output light of a narrow band of wavelength. Hence, light of the wavelength of a plurality of colors becomes necessary when solid-state light sources are used for illumination. Therefore, it becomes necessary to prepare a plurality of types of narrow band light sources with different light emission wavelengths and to output the light emitted from these light sources while always making the color constant.

For example, JP 2002-122794 A (PTL 1) discloses a method for controlling the spectroscopic properties of a light source for an electronic endoscope. Specifically, with this method, an image of a white object illuminated by an RGB full-color LED is first detected by a color single-layer imaging device provided at the tip of the electronic endoscope. Next, each detected color signal is input into a comparison circuit of a light source unit through a processing circuit. The signal amplitude level of each color signal is then compared in the comparison circuit. An LED driver that controls each light emission output of the full-color LED is controlled on the basis of the comparison result. The ratio between the signal amplitude level of each color signal detected in the color single-layer CCD is thus adjusted to become one. In this method, an appropriate color image can be captured regardless of the wavelength sensitivity characteristics of the color CCD used in the electronic endoscope.

CITATION LIST

Patent Literature

PTL 1: JP 2002-122794 A

SUMMARY

An illumination apparatus according to this disclosure includes:
a light source unit including a plurality of narrow band light sources with different peak wavelengths, the plurality of narrow band light sources being divided by peak wavelength into a plurality of narrow band light source groups, and each narrow band light source group that includes a plurality of the narrow band light sources being designated as a type one narrow band light source group;
a detector configured to detect an illumination color of illumination light obtained by light emission of the light source unit;
a memory configured to store a first appropriate illumination color for each type one narrow band light source group;
an output calculator configured, for each type one narrow band light source group, to compare the first appropriate illumination color of the type one narrow band light source group with the illumination color detected by the detector upon the plurality of narrow band light sources belonging to the type one narrow band light source group emitting light and to calculate an appropriate output for each narrow band light source belonging to the type one narrow band light source group; and
a light source controller configured to control the plurality of narrow band light sources included in the light source unit on a basis of the appropriate output calculated by the output calculator.

For each type one narrow band light source group, the output calculator may calculate the appropriate output of each narrow band light source belonging to the type one narrow band light source group so that the illumination color detected by the detector approaches the first appropriate illumination color of the type one narrow band light source group.

An endoscopic system according to this disclosure includes an endoscope, the endoscope including:
the aforementioned illumination apparatus; and
an imaging unit configured to convert returning light returning from an observed part to an image signal, the returning light being produced by illumination light emitted from the illumination apparatus.

The imaging unit may also function as the detector, and the detector may detect an image signal acquired for each type one narrow band light source group as the illumination color of the type one narrow band light source group.

With a standard subject disposed at the observed part, the detector may detect an image signal of the standard subject as the illumination color of the type one narrow band light source group, the image signal being acquired for each type one narrow band light source group.

Alternatively, the detector may detect the illumination color on a basis of a branched portion of illumination light branched from the illumination light emitted by the light source unit.

The illumination light emitted from the illumination apparatus upon causing the narrow band light sources belonging to the plurality of narrow band light source groups to emit light may be designated as observation illumination light;
the memory may further store a second appropriate illumination color; and
after calculating the appropriate output for each of the plurality of narrow band light sources in each type one narrow band light source group, the output calculator may calculate output of each narrow band light source belonging to each of the plurality of narrow band light source groups, while maintaining an output ratio of the appropriate output of each narrow band light source belonging to a same type one narrow band light source group, so that the observation illumination light approaches the second appropriate illumination color.

The second appropriate illumination color may be obtained by combining the plurality of narrow band light source groups; and the output calculator may calculate output of each narrow band light source belonging to the plurality of narrow band light source groups so that the observation illumination light has an illumination color substantially identical to the second appropriate illumination color.

The imaging unit may include a plurality of color light receiving elements having different wavelength sensitivity characteristics; and a plurality of narrow band light sources belonging to a same type one narrow band light source group may have peak wavelengths in a same wavelength region among a plurality of non-overlapping wavelength regions.

Alternatively, the imaging unit may include a plurality of color light receiving elements having different wavelength sensitivity characteristics; and a plurality of narrow band light sources belonging to a same type one narrow band light source group may have peak wavelengths in a plurality of different, non-overlapping wavelength regions.

At least one type one narrow band light source group may include a narrow band light source used during special light observation.

At least a portion of a surface of the standard subject facing the imaging unit may have a white region.

In the aforementioned endoscopic system, it may be that $N \geq L$ and $N \geq M$, where L, M, and N are natural numbers equal to or greater than one, L is a number of the narrow band light source groups, M is a maximum number of narrow band light sources belonging to any of the narrow band light source groups, and N is a number of types of colors of the color light receiving elements.

The number of the narrow band light sources included in the illumination apparatus is preferably at least four and no greater than nine.

The light source unit may simultaneously emit light from the narrow band light sources belonging to the narrow band light source groups sequentially by narrow band light source group, and the imaging unit may acquire the image signal in conjunction with a timing of light emission of the narrow band light sources and generate a color image on a basis of the image signal.

In this case, a portion of a surface of the standard subject facing the imaging unit may be divided into regions having three or more different colors.

A color correction apparatus according to this disclosure is for performing color correction of a light source apparatus, the light source apparatus including a plurality of narrow band light sources with different peak wavelengths, the plurality of narrow band light sources being divided by peak wavelength into a plurality of narrow band light source groups, and each narrow band light source group that includes a plurality of, the narrow band light sources being designated as a type one narrow band light source group, the color correction apparatus including:

a detector configured to detect an illumination color of illumination light obtained by light emission of the light source apparatus;

a memory configured to store an appropriate illumination color for each type one narrow band light source group; and an output calculator configured, for each type one narrow band light source group, to compare the first appropriate illumination color of the type one narrow band light source group with the illumination color detected by the detector upon the plurality of narrow band light sources belonging to the type one narrow band light source group emitting light and to calculate an appropriate output for each narrow band light source belonging to the type one narrow band light source group.

DETAILED DESCRIPTION

When using a narrow band light source, such as an LED or a laser, for illumination light, the wavelength or the amount of light shifts for each individual light source or shifts over time, which may lead to a change in the output image. In practice, LEDs and lasers vary individually from the central wavelength by approximately ±5 nm, or approximately ±10 nm in the case of large light sources. A light source having a broad spectrum, such as a xenon light source or a halogen light source, includes a large amount of light over a wide wavelength range. Therefore, in the case of such a light source, little variation occurs in terms of information being lost or overemphasized even if the wavelength shifts as described above. Conversely, image information that can be acquired by the aforementioned narrow band light sources is based on wavelength information of a single wavelength. Therefore, the image suffers a relatively large change as a result of individual wavelength variation or light amount variation in these light sources.

Therefore, in the context of an illumination apparatus and an endoscopic system that use a plurality of narrow band light sources, it would be helpful to provide an illumination apparatus that can irradiate illumination light having stable color even when the wavelength or amount of light varies in individual narrow band light sources, an endoscopic system using this illumination apparatus, and a color correction apparatus.

This disclosure provides an illumination apparatus that allows natural observation with high color reproduction by causing a laser light source group of a plurality of wavelengths to emit light. This disclosure also provides an endoscopic system that includes this illumination apparatus and provides a color correction apparatus. A "narrow band light source" as used herein refers to a light source having a wavelength intensity in a particular, narrow region and includes lasers, LEDs, and the like. In the embodiments, lasers are used as examples, but similar effects are also obtained with LEDs that similarly emit light of a narrow band spectrum. "Color" refers to the way a color appears. In particular, when mixing two or more types of light with different wavelengths, the color is the color observed when the generated light irradiates a white object. Furthermore, when counting lasers in this disclosure, lasers with different wavelengths are counted as separate lasers, whereas a plurality of lasers with the same wavelength provided for reasons such as improving the output at one wavelength, reducing speckles, or cutting costs are not counted separately. The same holds for LEDs as well.

Embodiments of this disclosure are described below with reference to the drawings.

Embodiment 1

Figure 1:
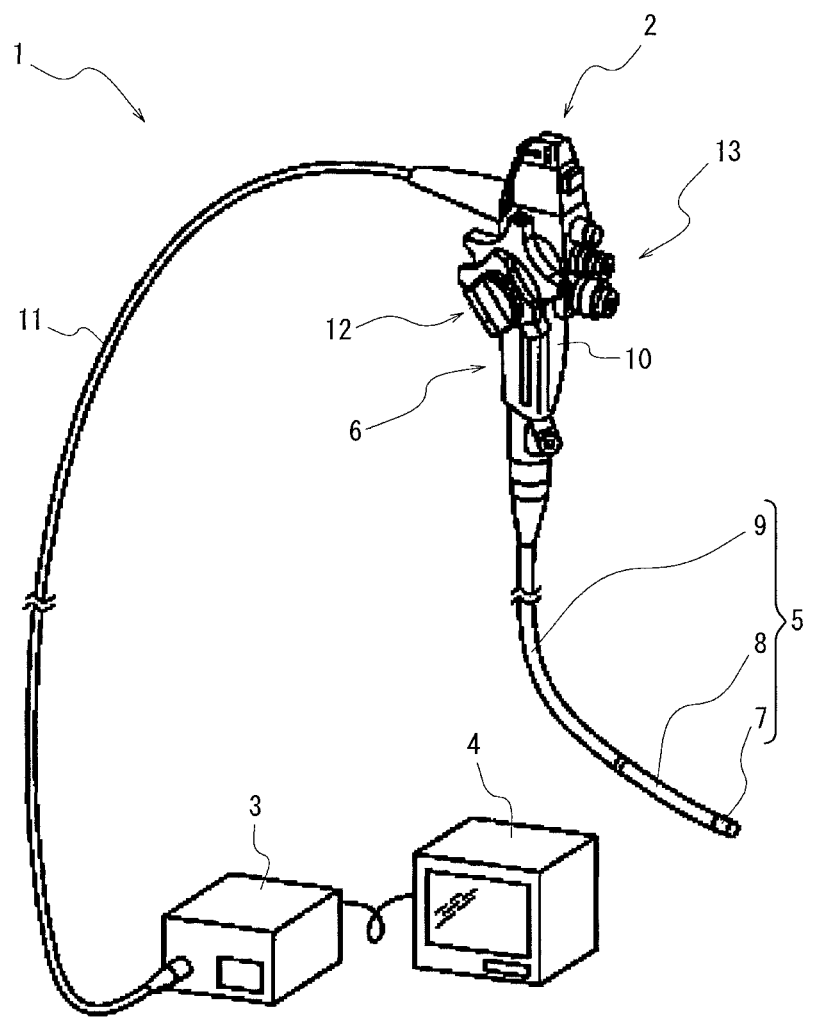
FIG. 1 is an external view of an endoscopic system according to Embodiment 1.
Figure 2:
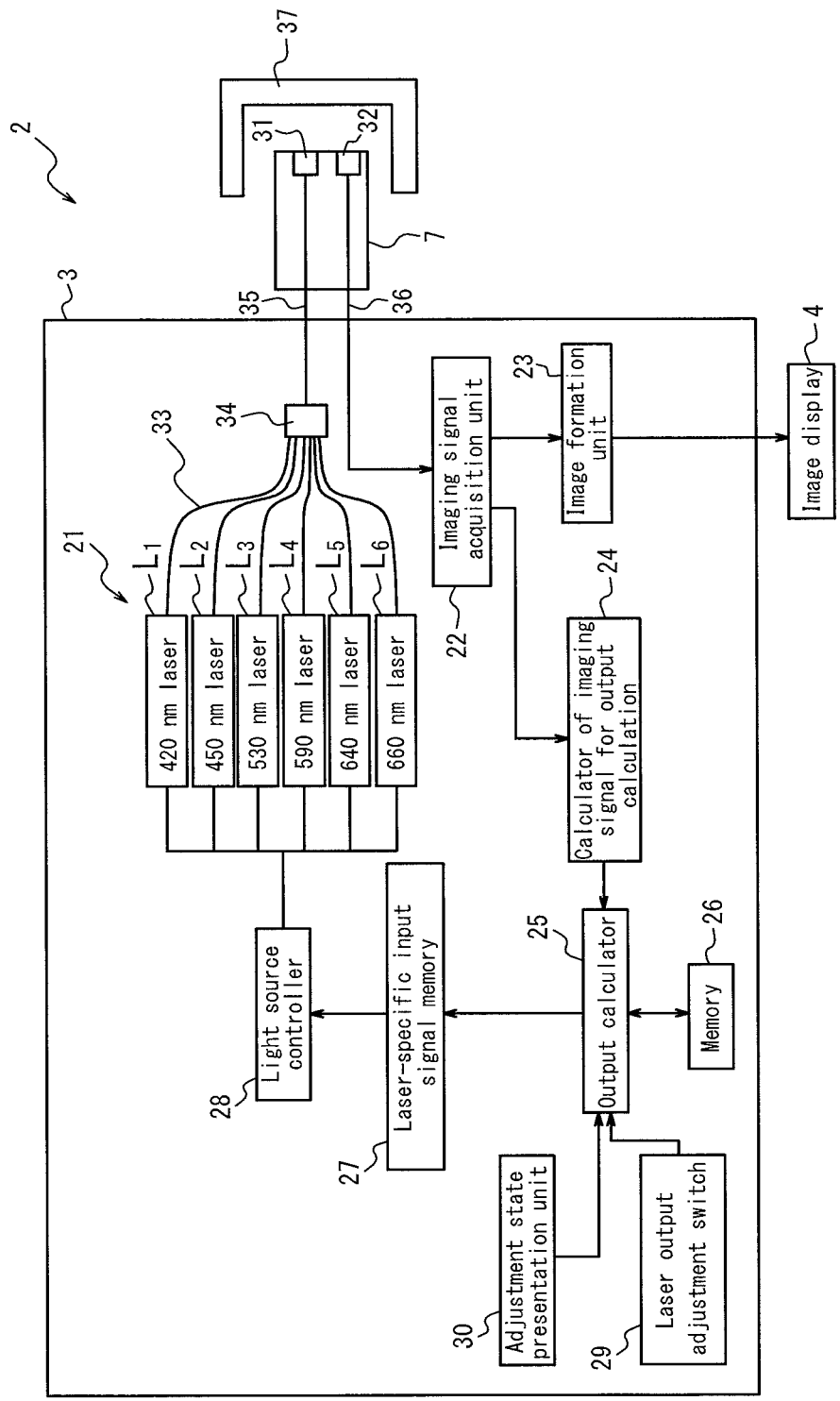
FIG. 2 is a block diagram of the main portion of the endoscopic system in FIG. 1.

FIG. 1 is an external view of an endoscopic system 1 according to Embodiment 1. FIG. 2 is a block diagram of the main portion related to this disclosure in the endoscopic system 1 of FIG. 1. As illustrated in FIG. 1, the endoscopic system 1 includes an endoscope 2, an endoscopic system body 3 connected detachably to the endoscope 2, and an image display 4 that displays an image captured by the endoscope 2.

The endoscope 2 includes an elongated insertion part 5 that is inserted into a body cavity and an operation part 6 provided at the opposite side (base end) from the tip of the insertion part 5 that is inserted into the body cavity. In order from the tip towards the base end, the insertion part 5 includes a rigid tip portion 7, a curved portion 8, and a flexible tube portion 9. The operation part 6 includes a grip 10, for gripping the endoscope 2, and a universal cord 11. A curved dial 12 for operating the curved portion 8 and a switch 13 for performing various operations during endoscope operation are provided on the grip 10.

As illustrated in FIG. 2, the endoscopic system body 3 of the endoscopic system 1 includes a light source unit 21, an imaging signal acquisition unit 22, an image formation unit 23, a calculator 24 of an imaging signal for output calculation, an output calculator 25, a memory 26, a laser-specific input signal memory 27, a light source controller 28, a laser output adjustment switch 29, and an adjustment state presentation unit 30. The imaging signal acquisition unit 22, image formation unit 23, calculator 24 of the imaging signal for output calculation, output calculator 25, memory 26, laser-specific input signal memory 27, and light source controller 28 may be implemented by one or a plurality of pieces of computer hardware having a processor and memory. A light distribution conversion member 31 and a color imaging unit 32 (detector) are provided in the rigid tip portion 7 of the endoscope 2.

The light source unit 21 includes six lasers $L_1$ to $L_6$ and a combiner 34. The lasers $L_1$ to $L_6$ have different wavelengths and are controlled individually by the light source controller 28. Solid-state lasers, such as semiconductor lasers, may be used as the lasers $L_1$ to $L_6$. The wavelengths of the lasers $L_1$ to $L_6$ are respectively 420 nm, 450 nm, 530 nm, 590 nm, 640 nm, and 660 nm. The light from the lasers $L_1$ to $L_6$ is guided by six optical fibers 33 to enter the combiner 34. In the combiner 34, the output of the optical fibers 33 from the aforementioned six lasers $L_1$ to $L_6$ is combined and output to one optical fiber 35. The six-wavelength mixed light that is concentrated in the one optical fiber 35 passes through the universal cord 11 of the endoscope 2 via the optical fiber 35 and is guided to the rigid tip portion 7 of the insertion part 5.

The light distribution conversion member 31 at the tip of the optical fiber 35 converts the six-wavelength mixed light guided through the optical fiber 35 into a light distribution that is appropriate for illumination and emits the result forward as illumination light. The light distribution conversion member 31 may be configured by a lens for expanding the diameter of the illumination light, a diffusion member that has a diffusing function for spatially equalizing the amount of light, a combination of such a lens and diffusion member, or the like.

During regular observation with the endoscopic system 1, the target of observation (observed part) is positioned ahead of the tip of the insertion part 5. The color imaging unit 32 is disposed on nearly the same surface as the light distribution conversion member 31. The color imaging unit 32 receives returning light from the target of observation two-dimensionally as a plane, converts an image of the object to an electric signal group as an image signal, and transmits the image signal to the endoscopic system body 3 over a signal line 36. The imaging signal acquisition unit 22 receives the transmitted image signal and relays the image signal to the image formation unit 23. The image formation unit 23 performs image processing for display, transmits the processed image signal to the image display 4, and displays an image with the image display 4. The image display 4 may, for example, be a monitor such as a liquid crystal display. The user of the apparatus can observe the target of observation by visually confirming the image.

Next, in the endoscopic system 1, the output balance adjustment in order to eliminate image quality variation caused by individual laser variation and imaging device sensitivity variation is described. In this embodiment, lasers with close oscillation wavelengths are designated as belonging to the same narrow band light source group, and the output balance is adjusted with lasers in a narrow band light source group in the same color region. When variation occurs in the amount of light or wavelength of the individual lasers $L_1$ to $L_6$, or when individual sensitivity variation occurs in the imaging device of the color imaging unit 32, the output ratio is adjusted with a set of lasers belonging to the same narrow band light source group so that the color imaging unit 32 obtains the same illumination color (the same signal output value). Individual variations thereby complement each other, allowing acquisition of a stable image signal.

Specifically, in order to stabilize each primary color constituting the color of the illumination light, the lasers are divided into wavelength regions. The lasers may be divided in accordance with the wavelength sensitivity characteristics of the imaging device in the color imaging unit 32. In the imaging device, typically primary color pixels having a plurality of different types of wavelength sensitivity characteristics are arranged in a regular pattern. More typically, three types of pixels are arrayed, i.e. pixels with red, green, and blue primary color filters disposed thereon.

Figure 3:
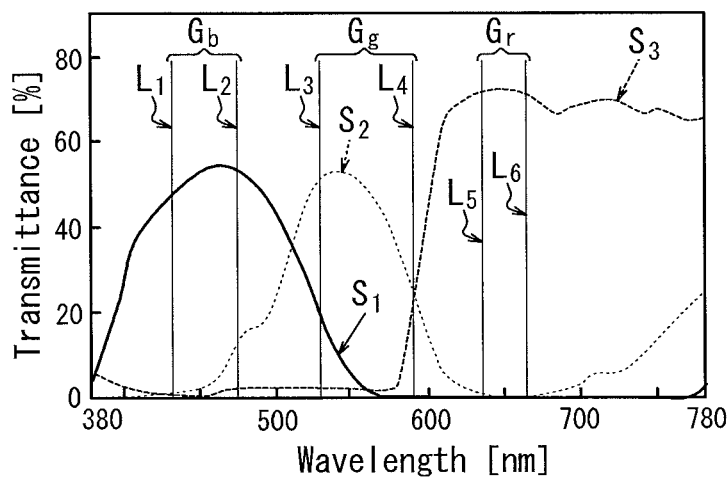
FIG. 3 illustrates the relationship between the wavelength sensitivity curve of the imaging device in the color imaging unit, the laser wavelength, and the narrow band light source groups.

FIG. 3 illustrates the relationship between wavelength sensitivity curves $S_1$ to $S_3$ for the imaging device in the color imaging unit 32, the laser wavelengths, and the narrow band light source groups Gr, Gg, Gb. In the wavelength sensitivity curves $S_1$ to $S_3$ in FIG. 3, the wavelength sensitivity curves for each of blue, green, and red in the imaging device are indicated by the spectral transmittance, for each color, of the color filter in the imaging device. In this way, the color imaging unit 32 includes color light receiving elements having different wavelength sensitivity characteristics. The vertical lines are lasers exhibiting a peak wavelength at the coordinate on the horizontal axis. The lasers are preferably grouped with the boundary between groups being the intersection, on the graph, where one of the wavelength sensitivity curves $S_1$ to $S_3$ becomes higher than other. In practice, however, it is difficult actually to measure the imaging device sensitivity characteristics. Therefore, a simple division may be adopted by setting the red narrow band light source group Gr to be a wavelength of 600 nm or greater, the green narrow band light source group Gg to be a wavelength of 500 nm or greater to less than 600 nm, and the blue narrow band light source group Gb to be a wavelength of less than 500 nm. In this way, in this embodiment, the lasers $L_1, L_2; L_3, L_4;$ and $L_5, L_6$ respectively belonging to the same narrow band light source groups Gb, Gg, and Gr have different peak wavelengths in the same wavelength region among a plurality of non-overlapping wavelength regions. In this disclosure, referring to lasers as "lasers $L_1, L_2; L_3, L_4;$ and $L_5, L_6$" or the like means that lasers $L_1$ and $L_2$, lasers $L_3$ and $L_4$, and lasers $L_5$ and $L_6$ are in respective groups.

In this embodiment, lasers belonging to the same narrow band light source group Gr, Gg, Gb complement each other's color. When imaging a subject of the same color/brightness, the RGB signal output from the color imaging unit 32 is adjusted to become a predetermined signal value even if the wavelength characteristics of the light source change or a different endoscope is used. This leads to stability of the image in each endoscopic apparatus and yields an image of the same color even between different endoscopic apparatuses. The signal value of the RGB image signal output from the imaging device for this color complementing is used as a parameter.

As described above, FIG. 3 illustrates grouping of light sources into narrow band light source groups Gr, Gg, Gb of different colors. In greater detail, lasers $L_1$ and $L_2$ belong to the blue narrow band light group Gb, lasers $L_3$ and $L_4$ belong to the green narrow band light group Gg, and lasers $L_5$ and $L_6$ belong to the red narrow band light source group Gr. Hereinafter, among narrow band light source groups, a narrow band light source group that includes a plurality of narrow band light sources is referred to as a type one narrow band light source group. Accordingly, a narrow band light source group that is formed by only a single narrow band light source is not a type one narrow band light source group.

The red narrow band light source group Gr, green narrow band light source group Gg, and blue narrow band light source group Gb are each type one narrow band light source groups.

Next, the method for output adjustment between lasers belonging to the same narrow band light source group is described. As illustrated in FIG. 2, the user first places a predetermined standard white board 37 at a predetermined distance and angle as a standard subject at the target of observation side of the tip of the insertion part 5. When the laser output adjustment switch 29 in the endoscopic system body 3 is pressed, then in accordance with a preset procedure, the lasers $L_1, L_2; L_3, L_4;$ and $L_5, L_6$ in the narrow band light source groups Gb, Gg, Gr generate output, and calculations to optimize each laser output are made internally.

In the case of this embodiment, for example the narrow band light source groups can be caused to produce output sequentially starting from the shortest wavelength. In other words, the lasers $L_1, L_2$ belonging to the blue narrow band light source group Gb, the lasers $L_3, L_4$ belonging to the green narrow band light source group Gg, and the lasers $L_5, L_6$ belonging to the red narrow band light source group Gr can be caused to emit light by narrow band light source group, and the narrow band light source groups Gb, Gg, Gr that emit light can be switched in sequence.

The illumination light emitted by each narrow band light source group (mixed wave of a plurality of lasers) is reflected by the standard white board 37. The resulting illumination color is detected from the standard white board 37 by the color imaging unit 32 as an image signal and is acquired by the imaging signal acquisition unit 22. The image signal from the imaging signal acquisition unit 22 is transmitted to the calculator 24 of the imaging signal for output calculation. The calculator 24 of the imaging signal for output calculation for example extracts the signal value (corresponding to the "illumination color") of a representative pixel, such as a predetermined center pixel, from within the image signal and outputs the signal value to the output calculator 25. The signal value acquired for each narrow band light source group is referred to as a current signal value and is represented as $Nr(r_{Rn}, g_{Rn}, b_{Rn})$, $Ng(r_{Gn}, g_{Gn}, b_{Gn})$, $Nb(r_{Bn}, g_{Bn}, b_{Bn})$ for the respective narrow band light source groups Gr, Gg, Gb. The "current signal value" is the signal value corresponding to the illumination color before adjustment of the illumination color.

The current signal values Nr, Ng, Nb are not limited to being a signal value obtained from a certain representative pixel and may instead be an average value, a peak value, or the like for the signal group obtained for a portion or all of the standard white board 37. By acquiring the current signal value for such a representative pixel or a particular portion, individual variation in the lasers or imaging device can be corrected stably.

Figure 4:
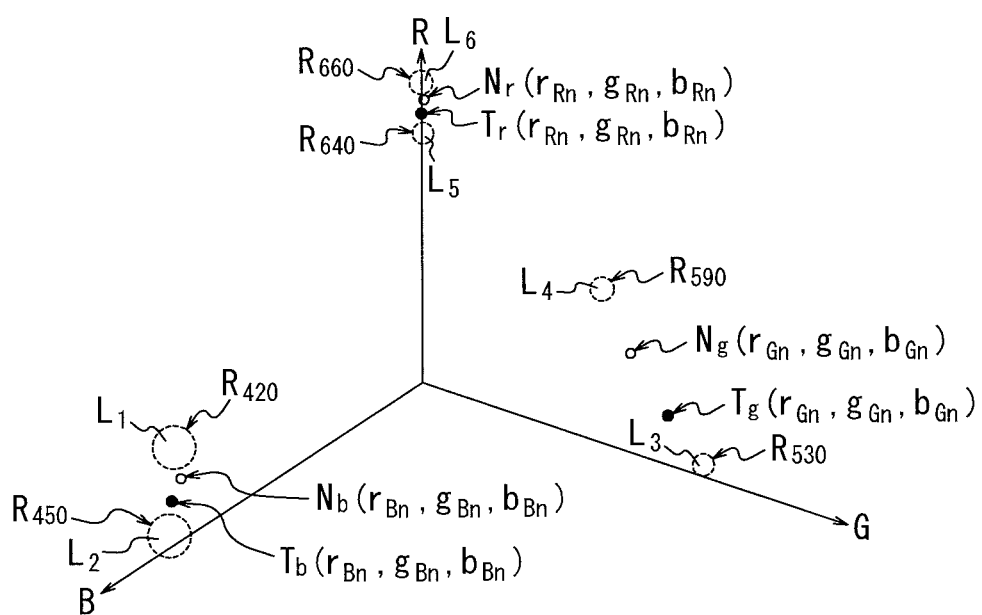
FIG. 4 illustrates color correction of each narrow band light source group in the RGB color space.

FIG. 4 illustrates color correction of the narrow band light source groups Gr, Gg, and Gb in the RGB color space. In FIG. 4, the range over which the RGB signal value of the lasers $L_1$ to $L_6$ is expected to vary is indicated by the regions $R_{420}, R_{450}, R_{530}, R_{590}, R_{640}, R_{660}$ surrounded by dashes. The memory 26 stores first appropriate illumination colors for the narrow band light source groups Gr, Gg, Gb as appropriate signal values $Tr(r_{Rt}, g_{Rt}, b_{Rt})$, $Tg(r_{Gt}, g_{Gt}, b_{Gt})$, $Tb(r_{Bt}, g_{Bt}, b_{Bt})$. The first appropriate illumination color is the color that should be represented by irradiation of illumination light from the narrow band light source groups Gr, Gg, Gb and is stored in the memory 26 as an appropriate image signal for each of the narrow band light source groups Gr, Gg, Gb. The first appropriate illumination colors for Gb, Gg, Gr are set to be within a range that allows adjustment even for the maximum variation among the expected wavelength variations in the output of the lasers $L_1$, $L_2$; $L_3$, $L_4$; and $L_5$, $L_6$ and in the imaging signal acquisition unit 22.

The output calculator 25 stores and executes a concrete calculation method to obtain the illumination light of the first appropriate illumination color by adjusting the output of each of the lasers $L_1$, $L_2$; $L_3$, $L_4$; and $L_5$, $L_6$ in the narrow band light source groups Gb, Gg, Gr.

For example, the current signal value $Nb(r_{Bn}, g_{Bn}, b_{Bn})$ of the narrow band light source group Gb upon simultaneous light emission by the laser $L_1$ (wavelength 420 nm) and laser $L_2$ (wavelength 450 nm) included in the blue narrow band light source group Gb is obtained from the calculator 24 of the imaging signal for output calculation. The output calculator 25 acquires/calculates this current signal value. The output calculator 25 also acquires the appropriate signal value $Tb(r_{Bt}, g_{Bt}, b_{Bt})$ for the blue narrow band light source group Gb from the memory 26. Next, the output calculator 25 compares the current signal value $Nb(r_{Bn}, g_{Bn}, b_{Bn})$ of the blue narrow band light source group Gb with the appropriate signal value $Tb(r_{Bt}, g_{Bt}, b_{Bt})$ and calculates the output of each of the lasers $L_1$, $L_2$. In greater detail, the output calculator 25 mathematically calculates the coordinate distance from the current signal value $Nb(r_{Bn}, g_{Bn}, b_{Bn})$ to the appropriate signal value $Tb(r_{Bt}, g_{Bt}, b_{Bt})$, performs a calculation in accordance with this distance, and calculates the appropriate output of the lasers $L_1$, $L_2$ so as to approach the appropriate signal value Tb (i.e. to approach the first appropriate illumination color). At this time, it is entirely possible that the output cannot be adjusted accurately to the appropriate signal value Tb. Therefore, the output calculator 25 adjusts the output of the lasers $L_1$, $L_2$ to become the closest signal value to the appropriate signal value on the coordinates of the RGB color space.

Figure 5:
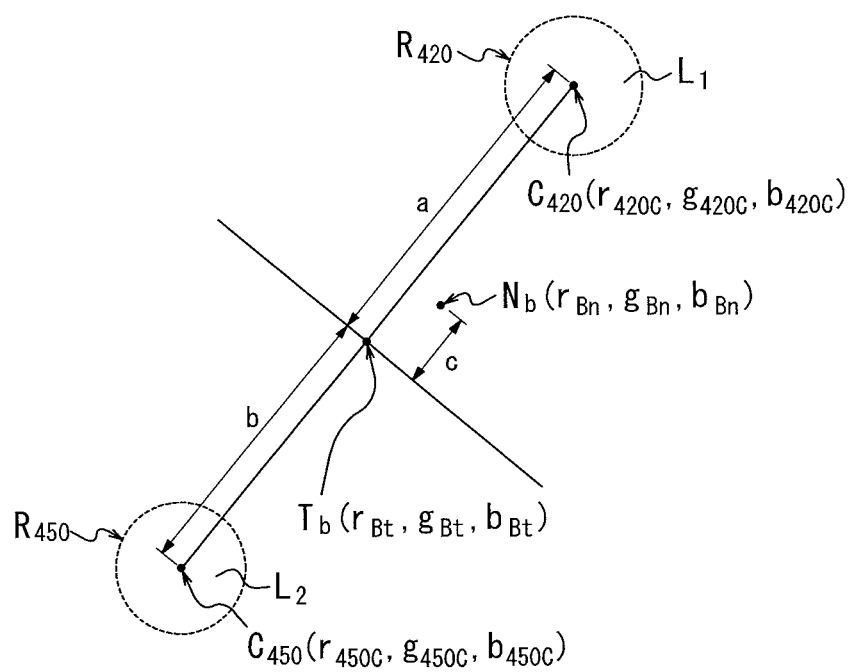
FIG. 5 illustrates color correction of the narrow band light source group in the blue region.

A concrete calculation method is described below with reference to FIG. 5, using the blue region as an example. FIG. 5 illustrates color correction of the blue narrow band light source group Gb, illustrating an enlargement of the blue portion in the RGB color space of FIG. 4.

The 420 nm band and 450 nm band lasers used in the lasers $L_1$, $L_2$ that belong to the blue narrow band light source group Gb vary in the RGB color space due to individual variation at the time of manufacturing and to change over time. The regions in the RGB color space over which these lasers vary are labeled $R_{420}$, $R_{450}$. The signal value, threshold current, and slope efficiency pertaining to the specification-centered lasers that are most often produced at the time of manufacturing are referred to as the central signal value, central threshold current, and central slope efficiency and are represented as follows for the 420 nm band laser and 450 nm band laser.

420 nm laser central signal value: $C_{420}(r_{420C}, g_{420C}, b_{420C})$
450 nm laser central signal value: $C_{450}(r_{450C}, g_{450C}, b_{450C})$
420 nm laser central threshold current: $I_{th420}$
450 nm laser central threshold current: $I_{th450}$
420 nm laser central slope efficiency: $\eta_{420}$
450 nm laser central slope efficiency: $\eta_{450}$ In general, it is most likely the case that a laser exhibiting the aforementioned central signal value can be acquired. Hence, the appropriate signal value $Tb(r_{Bt}, g_{Bt}, b_{Bt})$ is preferably set along a line connecting these central signal values. The lasers $L_1$ and $L_2$ are adopted from among 420 nm band lasers and 450 nm band lasers. Before adjustment, the output method with the highest expectation of the mixed light from the lasers $L_1$, $L_2$ becoming the appropriate signal value is to set the output of the lasers $L_1$, $L_2$ to the ratio between i) the distance from the 420 nm laser central signal value $C_{420}$ to the appropriate signal value Tb ("a" in FIG. 5) and ii) the distance from the 450 nm laser central signal value $C_{450}$ to the appropriate signal value Tb ("b" in FIG. 5). Accordingly, it is expected that the output of the laser $L_1$ will become "a×proportionality constant m" [mW], and the following is input as the current to laser $L_1$.

$$I_{th420} + a \times \text{proportionality constant } m \div \eta_{420} \quad (1)$$

It is expected that the output of the laser $L_2$ will become "b×proportionality constant m" [mW], and the following is input as the current to laser $L_2$.

$$I_{th450} + b \times \text{proportionality constant } m \div \eta_{450} \quad (2)$$

The signal value output in this way becomes the current signal value $Nb(r_{Bn}, g_{Bn}, b_{Bn})$.

In the RGB color space, a line orthogonal to the line that passes through the appropriate signal value Tb and connects the 420 nm laser central signal value $C_{420}$ and the 450 nm laser central signal value $C_{450}$ is designated an appropriate signal value orthogonal line. The coordinate distance in the RGB color space between the appropriate signal value orthogonal line and the current signal value Nb is then calculated ("c" in FIG. 5). In the example in FIG. 5, the current signal value Nb is on the 420 nm band laser side of the appropriate signal value orthogonal line. Therefore, the output can be brought closer to the appropriate signal value Tb by reducing the output of the laser $L_1$ and increasing the output of the laser $L_2$. Specifically, the applied current of the lasers $L_1$ and $L_2$ is reduced on the basis of the distance c. The applied current of the 420 nm band laser $L_1$ is changed to the following value:

$$I_{th420} + (a-c) \times \text{proportionality constant } m \div \eta_{420} \quad (3),$$

the applied current of the 450 nm band laser $L_2$ is changed to the following value:

$$I_{th450} + (b+c) \times \text{proportionality constant } m \div \eta_{450} \quad (4),$$

and the lasers $L_1$ and $L_2$ are caused to emit light.

In this way, the appropriate laser output ratio is determined for the lasers $L_1$, $L_2$ belonging to the blue narrow band light source group Gb, and the signal value when the lasers $L_1$, $L_2$ produce output simultaneously (optimized output signal value) is predicted. The output ratio of the lasers $L_3$, $L_4$; $L_5$, $L_6$ belonging to the other green and red narrow band light source groups Gg, Gr can be determined by the same method, and the optimized output signal values can be predicted.

As long as the distance in the RGB color space between the optimized output signal value and the appropriate signal value Tb is within 10% of the distance between the 420 nm laser central signal value $C_{420}$ and the 450 nm laser central signal value $C_{450}$, the difference in color between the illumination color based on the optimized output signal and the first appropriate illumination color is extremely small. Accordingly, a greater effect can be obtained by setting the optimized output signal value within this range.

Figure 6:
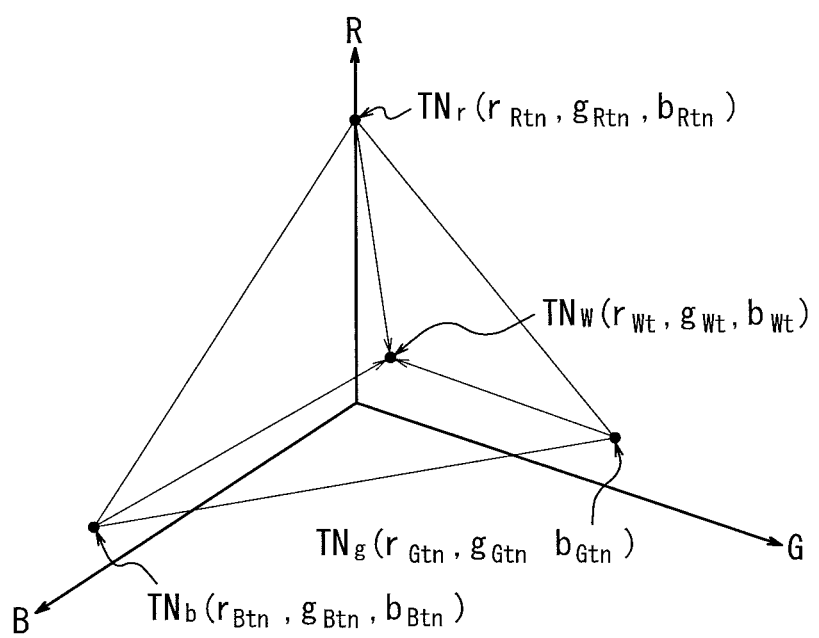
FIG. 6 illustrates white balance adjustment in the RGB color space.

Next, a method for adjusting the output ratio of all of the lasers $L_1$ to $L_6$ that produce output during regular light observation is described with reference to FIG. 6. FIG. 6 illustrates white balance adjustment in the RGB color space.

First, with the standard white board 37 in position, the lasers belonging to each of the narrow band light source groups Gr, Gg, Gb are caused to produce output from the light source unit 21 at the output ratios optimized for each of the narrow band light source groups Gr, Gg, Gb. The color imaging unit 32 then acquires the imaging signal with the imaging signal acquisition unit 22. As a result, the pixel signal value of each color as optimized within each narrow band light source group Gr, Gg, Gb is acquired. This is referred to as the measured optimized signal value of the narrow band light source group and is denoted as TNr($r_{Rtm}$, $g_{Rtm}$, $b_{Rtm}$), TNg($r_{Gtm}$, $g_{Gtm}$, $b_{Gtm}$), TNb($r_{Btm}$, $g_{Btm}$, $b_{Btm}$) respectively for the red, green, and blue colors. The appropriate signal values Tr, Tg, Tb of the narrow band light source groups and the measured optimized signal values TNr, TNg, TNb of the narrow band light source groups do not necessarily match.

On the other hand, the memory 26 stores an appropriate regular light signal value TNw($r_{Wt}$, $g_{Wt}$, $b_{Wt}$) as a "second appropriate illumination color" representing the appropriate observation illumination color upon simultaneous light emission by all of the narrow band light source groups used to emit light during observation. Similar to the aforementioned adjustment of the lasers within the narrow band light source groups Gr, Gg, Gb, the output calculator 25 calculates the distance from the measured optimized signal values TNr, TNg, TNb of the narrow band light source groups to the appropriate regular light signal value TNw. On the basis of this distance, the output calculator 25 calculates the output value of the narrow band light source groups Gr, Gg, Gb so that the resulting illumination color becomes substantially identical to the second appropriate illumination color. The resulting illumination color refers to the illumination color when observation illumination light is irradiated on the standard white board 37 upon the lasers $L_1$ to $L_6$ in all of the narrow band light source groups Gr, Gg, Gb emitting light. At this time, it is important that the output ratio of the lasers $L_1$, $L_2$; $L_3$, $L_4$; and $L_5$, $L_6$ within the narrow band light source groups Gb, Gg, Gr be maintained without change. As a result, the output ratio of the lasers $L_1$ to $L_6$ is determined.

In this context, "substantially identical" refers to how, in each coordinate direction in the RGB color space, the distance between the appropriate regular light signal value TNw($r_{Wt}$, $g_{Wt}$, $b_{Wt}$) and the signal value of the illumination light resulting from the mixed wave of the lasers $L_1$ to $L_6$ is within 5% of an average value of the distances between the appropriate regular light signal value TNw($r_{Wt}$, $g_{Wt}$, $b_{Wt}$) and the appropriate signal values Tb, Tg, Tr for each color. If the difference is of this magnitude, the visible color difference is small.

Next, the output calculator 25 outputs an input signal corresponding to the output ratio of each of the lasers $L_1$ to $L_6$ to the laser-specific input signal memory 27. The laser-specific input signal memory 27 stores this input signal. On the basis of the input signal of the lasers $L_1$ to $L_6$ stored in the laser-specific input signal memory 27, the light source controller 28 causes the lasers $L_1$ to $L_6$ of the light source unit 21 to produce output at the optimized output value. The output calculator 25 confirms that the detected signal is within a predetermined range of the appropriate regular light signal value TNw and terminates adjustment of the output ratio of the lasers $L_1$ to $L_6$. The output calculator 25 notifies the adjustment state presentation unit 30 that adjustment has terminated. The adjustment state presentation unit 30 then notifies the user of this termination by means such as a display or sound.

During subsequent regular observation by the endoscopic system 1, the input signal values stored in the laser-specific input signal memory 27 are used.

As described above, in order to correct the illumination color of the light source unit 21 in this embodiment, the output of each of the narrow band light source groups Gb, Gg, Gr is first adjusted. At this time, using the standard white board 37, the lasers $L_1$ to $L_6$ belonging to the narrow band light source groups Gb, Gg, Gr of the light source unit 21 are simultaneously caused to emit light. So that the illumination color obtained from the color imaging unit 32 approaches the first appropriate illumination color, the appropriate output is calculated for each of the lasers $L_1$, $L_2$; $L_3$, $L_4$; and $L_5$, $L_6$ belonging to the narrow band light source groups. As a result, it becomes possible to irradiate illumination light with a color that is stable with respect to the wavelength variation of individual lasers and variation in the amount of light over time. Regular illumination light composed of primary colors with stable color and brightness can thus be irradiated by each apparatus, color rendering properties can be stabilized, and images that are stable across apparatuses can be acquired.

Also, while ensuring that the output ratio between lasers within the same group does not change for the lasers $L_1$, $L_2$; $L_3$, $L_4$; and $L_5$, $L_6$ of the narrow band light source groups Gb, Gg, Gr, the output of the narrow band light source groups Gb, Gg, Gr is adjusted so that the illumination color when the observation illumination light is irradiated on the standard white board 37 becomes substantially identical to the second appropriate illumination color. Therefore, primary colors with stable color obtained from the narrow band light source groups Gb, Gg, Gr are combined, and a white illumination color nearly equivalent to the second appropriate illumination color is obtained. As a result, an image with stable color and good color rendering properties can be obtained regardless of the time of observation. Also, since the color is adjusted to become the predetermined second appropriate illumination color, the difference between individual lasers and the change over time have little effect.

Furthermore, conventionally variation in the wavelength sensitivity characteristics has also existed for each individual imaging device of the color imaging unit 32, and for each different imaging device, a change has occurred in the color of the acquired image. According to this embodiment, however, the same color imaging unit 32 that is used for image observation in the endoscopic system is also used to adjust the color of the illumination light. Therefore, the white balance can be adjusted by simultaneously taking into account differences in color based not only on the lasers $L_1$ to $L_6$ but also based on individual differences in the color imaging unit 32.

With regard to the peak wavelength of the narrow band light sources, "different wavelengths" refers to lasers having peak wavelengths that are at least 10 nm apart on the spectrum. The reason is that many of the visible light Laser Diodes (LDs) that are now being generally sold have specifications with a tolerance of 10 nm. Hence, providing a light source with a significantly different wavelength implies a laser with a wavelength difference of at least this tolerance. Also, in the Japanese Industrial Standards (JIS), the wavelength data interval when discussing color rendering properties, illumination color, and the like is often 5 nm. Therefore, in order to install a different wavelength light source with a different color, only an interval that is twice this amount, i.e. 10 nm or greater, is considered significant.

A variety of modifications and changes may be made to this embodiment. One such example is now described.

Figure 7:
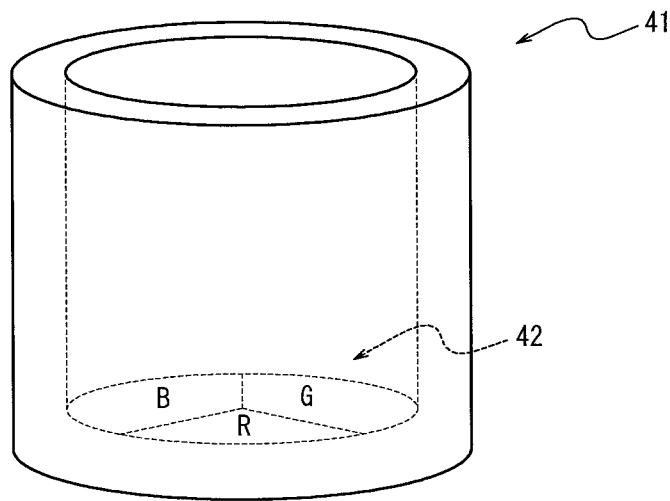
FIG. 7 illustrates an example of a color subject.

First, in the above embodiment, a color correction method (synchronous method) has been discussed, whereby illumination light is irradiated nearly simultaneously onto the standard white board 37 in an endoscopic apparatus in which RGB primary color filters exist within the imaging device of the color imaging unit 32. The method for color correction, however, is not limited to this case. For example, another method (color interleaving) is known for use when no color filter exists on the front surface or the like of the imaging device, so that the imaging device only receives luminance information. By the light source controller 28 controlling the light source unit 21, each of the RGB colors is irradiated sequentially in time. An image signal is acquired by the imaging unit in accordance with the timing of light emission by each color light source, and the image of the subject is colorized. In this case, the output of the narrow band light source groups Gr, Gg, Gb corresponding to the RGB colors that are sequentially output is preferably adjusted. Unlike the color imaging unit 32, however, since the signal output from the imaging device is only a luminance signal in this case, the solution to optimization cannot be unambiguously determined. The standard subject thus needs to be colorized. Therefore, instead of the standard white board 37 in the above embodiment (synchronous method), a color standard subject 41 is used, an example of which is illustrated in FIG. 7. In the color standard subject 41, a subject surface 42 is divided into three parts, which are respectively colored red (R), blue (B), and green (G). A monochrome signal value group capturing a predetermined portion of each color of the color standard subject 41 is designated as representative pixels, thus allowing color correction to be performed in the same way as the above embodiment. The subject surface of the color standard subject 41 may also be divided into four or more parts, and each part may be colored a different color.

Figure 8:
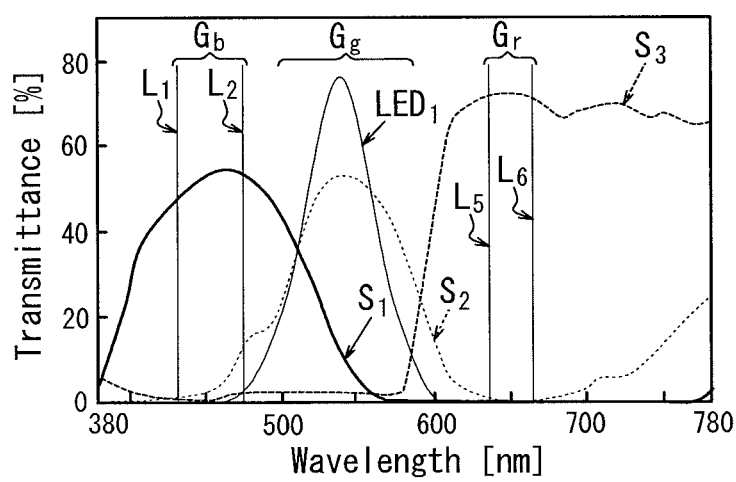
FIG. 8 illustrates the relationship between the wavelength sensitivity curves of the imaging device, the wavelengths of the narrow band light sources, and the narrow band light source groups in the case of using only an LED in the narrow band light source group of the green region.

In the above embodiment, the case of all of the narrow band light sources being lasers has been described, but the configuration of the light source unit 21 is not limited to this case. For example, with regard to the green region, a light source other than lasers may be used, such as LEDs or fluorescent material. FIG. 8 illustrates the relationship between the wavelength sensitivity curves $S_1$ to $S_3$ of the imaging device, the wavelengths of the narrow band light sources, and the narrow band light source groups Gr, Gg, Gb in the case of using only $LED_1$, which is a green LED, in the narrow band light source group Gg of the green region. In such a case, the output ratio is not adjusted within the narrow band light source group Gg. Rather, the color of the light source $LED_1$ is acquired as a signal for the green narrow band light source group Gg. During adjustment of the white balance for regular observation, the light amount ratio is adjusted so as to obtain the appropriate regular light signal value TNw. In this example, the green narrow band light source group Gg is not a type one narrow band light source group, but the red and blue narrow band light source groups Gr, Gb are type one narrow band light source groups.

Figure 9:
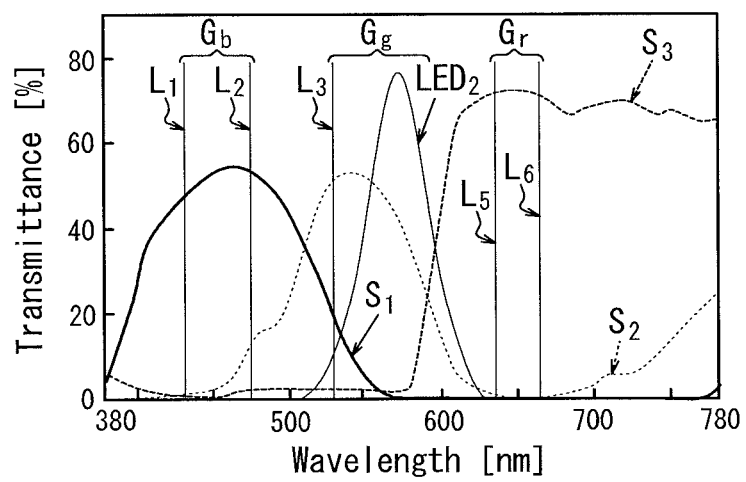
FIG. 9 illustrates the relationship between the wavelength sensitivity curves of the imaging device, the wavelengths of the narrow band light sources, and the narrow band light source groups in the case of using an LED and a laser in the narrow band light source group of the green region.

FIG. 9 illustrates the relationship between the wavelength sensitivity curves $S_1$ to $S_3$ of the imaging device, the wavelengths of the narrow band light sources, and the narrow band light source groups Gr, Gg, Gb in the case of using an LED and a laser in the narrow band light source group Gg of the green region. As illustrated in FIG. 9, it may also be the case that a laser $L_3$ and an $LED_2$, which is a green LED, are mixed in the green region. In this case, since it is necessary to correct the green LED and the green laser $L_3$, color correction is performed for both light sources. An example of the green laser being the same laser $L_3$ as in the above embodiment is illustrated, but the laser that is combined with the green LED may be a different green laser. In this example, the green narrow band light source group Gg is a type one narrow band light source group.

The maximum number of narrow band light source groups and of lasers belonging to each narrow band light source group is preferably equal to or less than the number of types of colors of the color light receiving elements in order to achieve a stable illumination color and to achieve stable color rendering properties. In other words, it is preferably the case that N≥L and N≥M, where L, M, and N are natural numbers equal to or greater than one, L is the number of narrow band light source groups, M is the maximum number of narrow band light sources belonging to any of the narrow band light source groups, and N is the number of types of colors of the color light receiving elements.

The reason is that in order for an unambiguous solution to be calculable for the output ratio that achieves the appropriate signal value with respect to a plurality of narrow band light sources, the number of narrow band light sources (lasers, LEDs, and the like) belonging to each narrow band light source group always needs to be equal to or less than the number of types of signals that are output from the color imaging unit. The number of types of signals output from the color imaging unit corresponds to the number of types of colors of the color light receiving elements in the color imaging unit. For example, in general the number of narrow band light sources belonging to each narrow band light source group is preferably three or less, which is the same as the number of types of colors (RGB) in the color imaging unit. If the number of narrow band light sources belonging to each narrow band light source group is four or greater, multiple solutions to the output ratio of the lasers that achieves the appropriate signal value may exist, and the color rendering properties may differ as a result.

On the other hand, the total number of narrow band light sources is preferably greater than the number of types of colors of the color light receiving elements. The reason is that if an apparatus for observation of regular light uses only the same number of lasers as the number of types of colors of the color imaging unit, there is no need for partial adjustment color by color. Since the number of types of colors is generally three as described above, the total number of narrow band light sources is preferably four or greater. Accordingly, in the case of a general color imaging device, the total number of narrow band light sources is preferably at least four and no greater than nine. By adopting this number, the output ratio of all of the narrow band light sources is solved unambiguously for each color, and the output ratio for achieving the second appropriate illumination color is solved unambiguously. Therefore, an observation apparatus that always has the same color and the same color rendering properties is achieved.

The narrow band light sources (lasers, LEDs, or the like) belonging to the narrow band light source groups Gr, Gg, Gb do not necessarily have to emit light "simultaneously". While the imaging device is receiving light as one frame, a plurality of narrow band light sources belonging to the same narrow band light source group may be caused to emit light sequentially, or a plurality of narrow band light sources may be caused to emit light sequentially frame by frame. In particular in the latter case, the output ratio that most closely approaches the appropriate signal color when the narrow band light sources emit light simultaneously is preferably calculated on the basis of narrow band light source information acquired for a plurality of frames.

Embodiment 2

Figure 10:
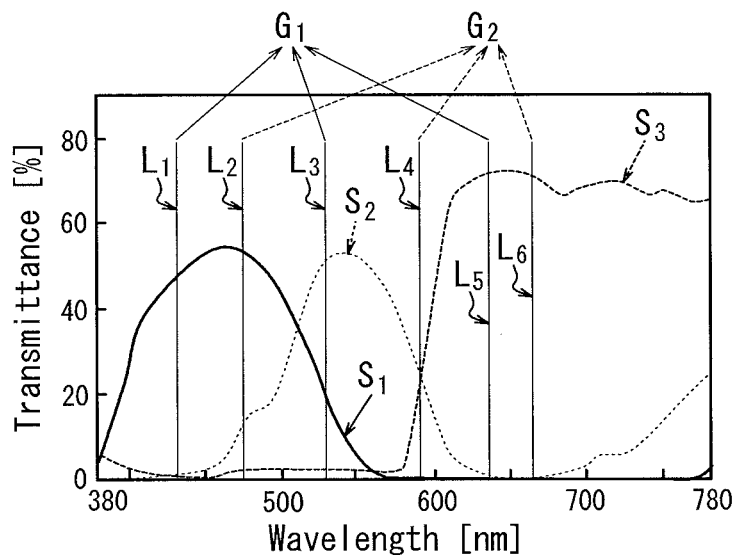
FIG. 10 illustrates the relationship between the wavelength sensitivity curves of the imaging device, the laser wavelengths, and the narrow band light source groups in Embodiment 2.

Embodiment 2 differs from the endoscopic system in Embodiment 1 by changing the way lasers are grouped, as illustrated in FIG. 10. The remaining configuration of the endoscopic system 1 is thus similar to the configuration of Embodiment 1 illustrated in FIG. 2. As in Embodiment 1, an example of using six lasers, i.e. laser $L_1$ (420 nm), laser $L_2$ (450 nm), laser $L_3$ (530 nm), laser $L_4$ (590 nm), laser $L_5$ (640 nm), and laser $L_6$ (660 nm), is described. The laser wavelengths are not limited to these examples, however, and a variety of lasers may be used.

In Embodiment 2, lasers $L_1$, $L_3$, $L_5$ belong to the first narrow band light source group $G_1$, and lasers $L_2$, $L_4$, $L_6$ belong to the second narrow band light source group $G_2$. This division is made as follows. First, the lasers $L_1$ to $L_6$ are grouped according to the wavelength sensitivity characteristics of the imaging device in the color imaging unit 32, so that the lasers $L_1$, $L_2$ are grouped as narrow band light sources belonging to the blue region, the lasers $L_3$, $L_4$ are grouped as narrow band light sources belonging to the green region, and the lasers $L_5$, $L_6$ are grouped as narrow band light sources belonging to the red region. Next, one laser from each color region is selected and regrouped to yield the above-described combinations. In other words, the lasers $L_1$, $L_3$, $L_5$; $L_2$, $L_4$, $L_6$ respectively belonging to the first and second narrow band light source groups $G_1$, $G_2$ have peak wavelengths in a plurality of different, non-overlapping wavelength regions.

The number of lasers is an integer multiple of the number of first and second narrow band light source groups $G_1$, $G_2$. One laser is preferably selected from the wavelength regions of each of the colors red, green, and blue, but the method for grouping lasers is not limited to this example. The first and second narrow band light source groups $G_1$, $G_2$ may be arranged so as not to include any laser having a peak wavelength in a certain wavelength region. Alternatively, a plurality of lasers may be selected from the same wavelength region. A plurality of lasers, however, must belong to each of the first and second narrow band light source groups $G_1$, $G_2$.

The following describes a method for adjusting output of the lasers $L_1$ to $L_6$.

As the target color (first appropriate illumination color) of the first and second narrow band light source groups $G_1$, $G_2$, the memory 26 stores the first and second appropriate signal values $T_{W1}(r_{W1t}, g_{W1t}, b_{W1t})$, $T_{W2}(r_{W2t}, g_{W2t}, b_{W2t})$ so as to yield a predetermined color in the narrow band light source groups $G_1$, $G_2$. The output calculator 25 can read these appropriate signal values $T_{W1}$, $T_{W2}$ from the memory 26.

Upon operation of the laser output adjustment switch 29 and the start of output adjustment processing, the light source controller 28 simultaneously causes the lasers $L_1$, $L_3$, $L_5$ belonging to the first narrow band light source group $G_1$ to emit light on the basis of an input signal stored in the laser-specific input signal memory 27. The standard white board 37 is placed at the end of the insertion part 5 of the endoscope 2, i.e. at the target of observation side, as in Embodiment 1. Returning light from the standard white board 37 is detected by the color imaging unit 32 and acquired by the imaging signal acquisition unit 22. Next, the calculator 24 of the imaging signal for output calculation acquires the first current signal value $N_{W1}(r_{W1n}, g_{W1n}, b_{W1n})$, which is the signal value of a representative pixel, such as the "center pixel", on the screen. Subsequently, the lasers $L_2$, $L_4$, $L_6$ belonging to the second narrow band light source group $G_2$ simultaneously emit light, and the calculator 24 of the imaging signal for output calculation acquires the second current signal value $N_{W2}(r_{W2n}, g_{W2n}, b_{W2n})$. The first current signal value $N_{W1}$ and second current signal value $N_{W2}$ are transmitted to the output calculator 25.

Figure 11:
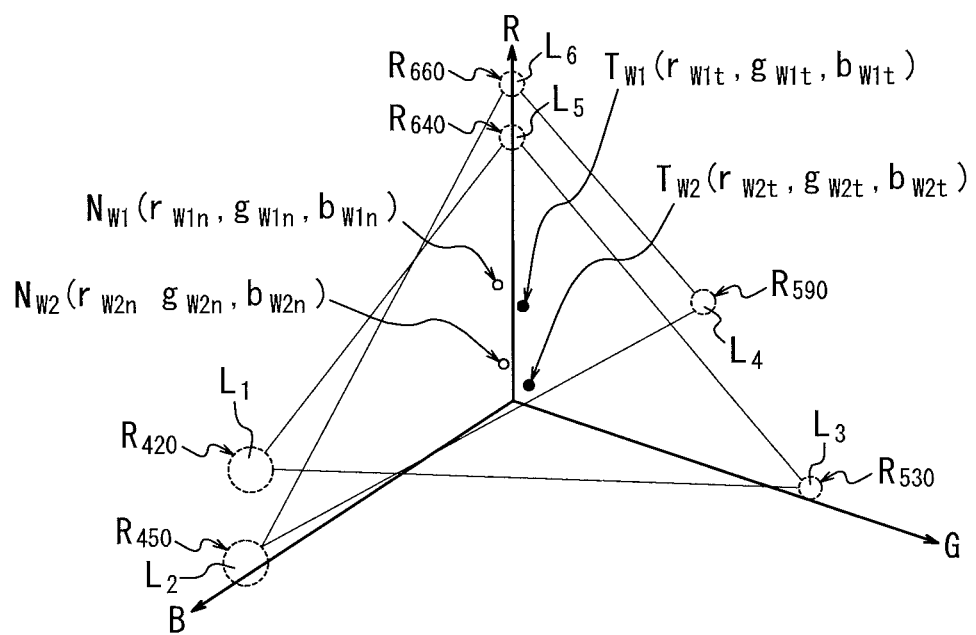
FIG. 11 illustrates color correction of each narrow band light source group in the RGB color space.

FIG. 11 illustrates color correction of the first and second narrow band light source groups $G_1$, $G_2$ in the RGB color space. As in FIG. 4, the regions $R_{420}$, $R_{450}$, $R_{530}$, $R_{590}$, $R_{640}$, $R_{660}$ surrounded by dashes indicate the regions in which the signal values of the respective lasers $L_1$ to $L_6$ are thought to vary in the RGB color space. The first and second appropriate signal values TW1, TW2 and the first and second current signal values $N_{W1}$, $N_{W2}$ are displayed in the RGB color space as illustrated in FIG. 11.

The output calculator 25 compares the current signal value $T_{W1}$ and the appropriate signal value $N_{W1}$ of the first narrow band light source group $G_1$ in the RGB color space and calculates the output ratio (appropriate laser output ratio) of the lasers $L_1$, $L_3$, $L_5$ belonging to the first narrow band light source group $G_1$ so that the output ratio minimizes the distance between the current signal value $T_{W1}$ and the appropriate signal value $N_{W1}$. The output calculator 25 then compares the current signal value $T_{W2}$ and the appropriate signal value $N_{W2}$ of the second narrow band light source group $G_2$ and calculates the output ratio (appropriate laser output ratio) of the lasers $L_2$, $L_4$, $L_6$ belonging to the second narrow band light source group $G_2$ so that the output ratio minimizes the distance between the current signal value $T_{W2}$ and the appropriate signal value $N_{W2}$.

Next, the output calculator 25 outputs the appropriate laser output ratio of each laser, as calculated for the first narrow band light source group $G_1$ and the second narrow band light source group $G_2$, to the laser-specific input signal memory 27. On the basis of this appropriate laser output ratio, the light source controller 28 controls the light source unit 21 and first causes the lasers $L_1$, $L_3$, $L_5$ in the first narrow band light source group $G_1$ to emit light at the calculated appropriate laser output ratio. As a result, the output calculator 25 acquires the optimized first measured signal value $TNw_1(r_{W1m}, g_{W1m}, b_{W1m})$ via the color imaging unit 32, imaging signal acquisition unit 22, and calculator 24 of the imaging signal for output calculation. Furthermore, the light source controller 28 causes the lasers $L_2$, $L_4$, $L_6$ in the second narrow band light source group $G_2$ to emit light at the calculated appropriate laser output ratio. As a result, the output calculator 25 acquires the optimized second measured signal value $TNw_2(r_{W2m}, g_{W2m}, b_{W2m})$ in the same way as above.

Figure 12:
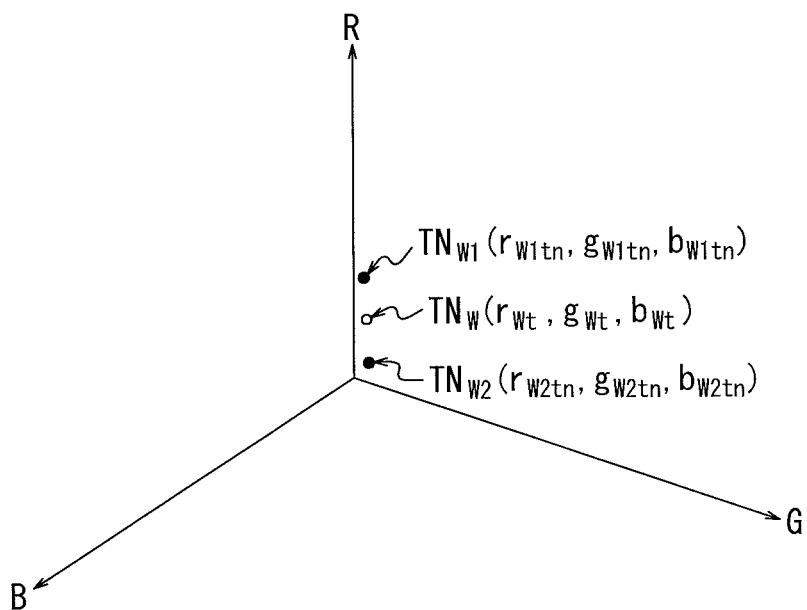
FIG. 12 illustrates white balance adjustment in the RGB color space.

On the other hand, as in Embodiment 1, the memory 26 stores an appropriate regular light signal value $TNw(r_{Wt}, g_{Wt}, b_{Wt})$ as a "second appropriate illumination color" upon simultaneous light emission by all of the narrow band light source groups used to emit light during observation. The first measured optimized signal value $TNw_1$, the second measured optimized signal value $TNw_2$, and the appropriate regular light signal value $TNw$ are represented as in FIG. 12 in the RGB color space. FIG. 12 illustrates white balance adjustment in the RGB color space.

Next, the output calculator 25 calculates the distance from each of the measured optimized signal values $TNw_1$ and $TNw_2$ of the narrow band light source groups to the appropriate regular light signal value $TNw$. On the basis of this distance, the output calculator 25 calculates the output values of the narrow band light source group $G_1$, G2 such that the illumination color upon the standard white board 37 being irradiated with observation illumination light when the lasers $L_1$, $L_3$, $L_5$; $L_2$, $L_4$, $L_6$ of the narrow band light source groups $G_1$, $G_2$ emit light becomes substantially identical to the second appropriate illumination color. Specifically, the output calculator 25 weights the average of the first measured optimized signal value $TNw_1$ and the second measured optimized signal value $TNw_2$ for the aforementioned distance and determines the output ratio between the narrow band light source groups $G_1$, $G_2$ so that this average is closest to the appropriate regular light signal value $TNw$. At this time, the output ratio of the lasers belonging to the narrow band light source groups $G_1$, $G_2$ are not changed.

With this approach, the lasers $L_1$, $L_3$, $L_5$; $L_2$, $L_4$, $L_6$ that have greatly different wavelengths in different wavelength regions are grouped in the narrow band light source groups $G_1$, $G_2$. As a result, the signal value (color) for the mixed light changes greatly when variation occurs in the amount of light or wavelength of the individual lasers $L_1$ to $L_6$, or when individual sensitivity variation occurs in the imaging device of the color imaging unit 32. Therefore, the output ratio of the lasers in each of the narrow band light source groups $G_1$, $G_2$ can be calculated easily and to a high degree of accuracy, thereby allowing the color of the mixed light to be stabilized rapidly.

Furthermore, by appropriately adjusting the output ratio of the first narrow band light source group $G_1$ and the second narrow band light source group $G_2$, a signal of an illumination color that is always identical or close can be obtained from the imaging device, and illumination light that always has a stable color and color rendering properties can be irradiated.

Embodiment 3

Figure 13:
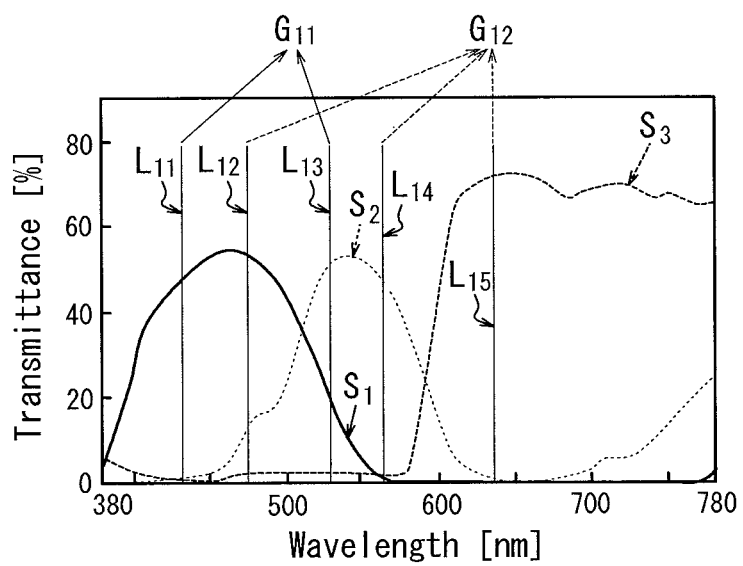
FIG. 13 illustrates the relationship between the wavelength sensitivity curves of the imaging device, the laser wavelengths, and the narrow band light sources groups in Embodiment 3.

This embodiment differs from the endoscopic system 1 in Embodiment 1 by dividing the lasers of each color for regular observation into a narrow band light source group of lasers also used for special light observation and a narrow band light source group of other lasers. FIG. 13 illustrates the relationship between wavelength sensitivity curves $S_1$ to $S_3$ for the imaging device, the laser wavelengths, and the narrow band light source groups $G_{11}$, $G_{22}$ in Embodiment 3. The configuration of the endoscopic system in Embodiment 3 is similar to the configuration of Embodiment 1 illustrated in FIG. 2, except for the lasers configuring the light source unit 21 and their grouping.

One of the major characteristics of multiband laser illumination using a plurality of laser light sources is that regular light observation with high color rendering properties can be performed using only lasers. An additional characteristic is that by causing only a portion of the lasers to emit light, it is easy to implement an emphasized observation method that emphasizes and displays a particular site, substance, component, or the like, which is generally called Narrow Band Imaging (NBI). In this embodiment, by partially adopting the aforementioned emphasized observation method for regular light images, a method for setting the laser output ratio is adopted to implement a technique that creates a user-friendly image in which a particular site, substance, component, or the like is emphasized in the regular light images.

Specifically, as illustrated in FIG. 13, the light source unit 21 of this endoscopic system 1 includes five lasers: $L_{11}$ (420 nm), $L_{12}$ (450 nm), $L_{13}$ (530 nm), $L_{14}$ (590 nm), and $L_{15}$ (640 nm). Among these lasers, the lasers $L_{11}$ and $L_{13}$ that are used for special light observation belong to a first narrow band light source group $G_{11}$, whereas the other lasers $L_{12}$, $L_{14}$, and $L_{15}$ belong to a second narrow band light source group $G_{12}$.

Figure 14:
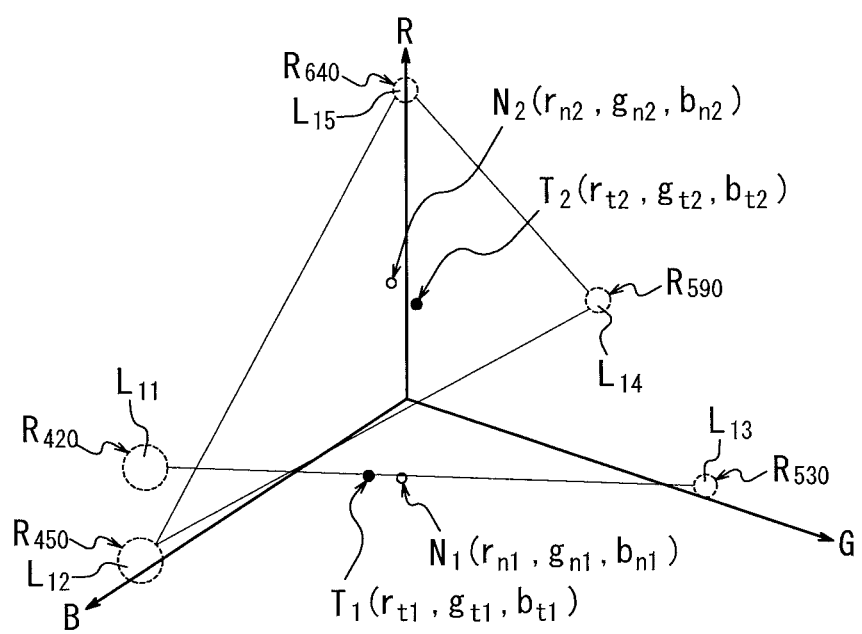
FIG. 14 illustrates color correction of each narrow band light source group in the RGB color space.

FIG. 14 illustrates color correction of each of the narrow band light source groups $G_{11}$, $G_{12}$ in the RGB color space. The regions $R_{420}$, $R_{450}$, $R_{530}$, $R_{590}$, $R_{640}$, $R_{660}$ surrounded by dashes indicate the regions in which the signal values of the respective lasers $L_{11}$ to $L_{15}$ are thought to vary in the RGB color space. The first narrow band light source appropriate signal value $T_1(r_{t1}, g_{t1}, b_{t1})$ and the second narrow band light source appropriate signal value $T_2(r_{t2}, g_{t2}, b_{t2})$ are signal values stored in the memory 26 so that the first and second narrow band light source groups $G_{11}$, $G_{12}$ yield a predetermined color.

Upon operation of the laser output adjustment switch 29, as in Embodiment 1 and Embodiment 2, the lasers belonging to the first narrow band light source group $G_{11}$ and the second narrow band light source group $G_{12}$ sequentially emit light at a predetermined output ratio. The first narrow band group current signal value $N_1(r_{n1}, g_{n1}, b_{n1})$ and the second narrow band group current signal value $N_2(r_{n2}, g_{nw}, b_{n2})$ are thus acquired. The output calculator 25 calculates the output ratio (appropriate laser output ratio) of the lasers $L_{11}$, $L_{13}$ belonging to the first narrow band light source group $G_{11}$ so as to minimize the distance between the current signal value T1 and the appropriate signal value N1 of the first narrow band light source group $G_{11}$ in the RGB color space. The output calculator 25 then similarly calculates the output ratio (appropriate laser output ratio) of the lasers $L_{12}$, $L_{14}$, $L_{15}$ belonging to the second narrow band light source group $G_{12}$ so as to minimize the distance between the current signal value T2 and the appropriate signal value N2 of the second narrow band light source group $G_{12}$.

Furthermore, as in Embodiments 1 and 2, the memory 26 stores an appropriate regular light signal value for adjusting the white balance, and as in Embodiments 1 and 2, the mutual output ratio of the first narrow band light source group $G_{11}$ and second narrow band light source group $G_{12}$ is calculated without changing the output ratio within the narrow band light source group. As a result, the output ratio of the lasers $L_{11}$ to $L_{15}$ is determined so that a signal value of substantially the same color as the appropriate regular light signal value is obtained.

As a result, the wavelengths 420 nm and 530 nm of the laser $L_{11}$ and laser $L_{13}$ included in the first narrow band light source group $G_{11}$ approach the representative absorption wavelength of hemoglobin. By causing these two lasers $L_{11}$, $L_{13}$ to irradiate a biological organism, the blood vessels can be emphasized in the display, thus yielding illumination light for special light observation. Depending on the output ratio of the lasers $L_{11}$ and $L_{13}$, a large difference occurs in the color of the image emphasizing blood vessels. Hence, color correction needs to be performed accurately. Creating an image in which a special light observation image is overlaid on an image yielded by irradiation of the lasers $L_{12}$, $L_{14}$, $L_{15}$ that do not emit illumination light for special light observation allows creation of a biological regular light image that has excellent color reproduction and that emphasizes a particular substance or the like.

According to this embodiment, a plurality of lasers $L_{11}$, $L_{13}$ having wavelengths that allow emphasis by special light observation and a plurality of lasers $L_{12}$, $L_{14}$, $L_{15}$ at other wavelengths are grouped respectively into narrow band light source groups $G_{11}$, $G_{12}$. Therefore, both the color of a regular light image and the color of a special light image overlaid thereon can be stabilized, and during image observation in which a special light observation image is overlaid, observation with excellent and more stable color rendering properties becomes possible.

Special light observation is not limited to Narrow Band Imaging (NBI) and includes all cases of using illumination light composed of only narrow band light that differs from white light to observe, emphasize some object, component, structure, or the like, and acquire an image. Examples include emphasizing blood vessels, displaying blood flow, displaying oxygen saturation, displaying arteries/veins, displaying autofluorescence, emphasizing drug fluorescence, and emphasizing irregularities.

Embodiment 4

Figure 15:
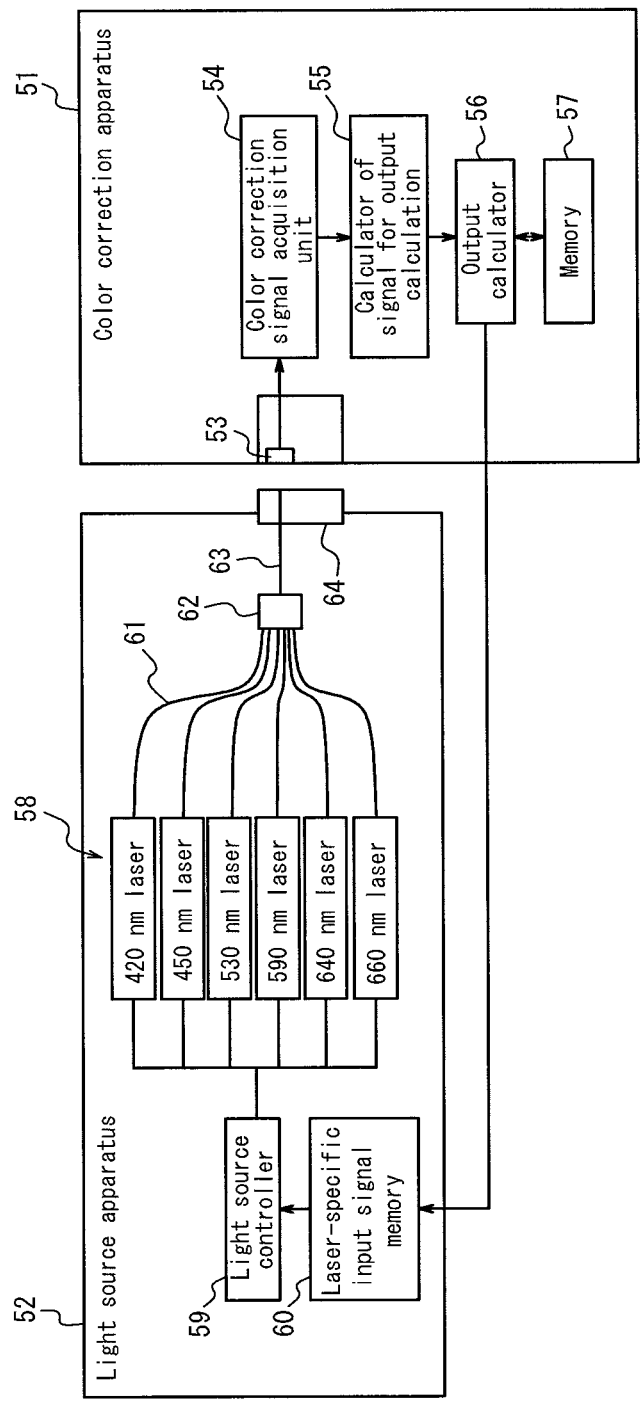
FIG. 15 is a block diagram illustrating a color correction apparatus according to Embodiment 4 along with a light source apparatus.

FIG. 15 is a block diagram illustrating a color correction apparatus 51 according to Embodiment 4 along with a light source apparatus 52. The color correction apparatus 51 corrects wavelength variation for example at the time of shipping of the light source apparatus 52. The oscillation wavelength of the laser in an endoscope and the light reception wavelength of an imaging device exhibit individual variation. When these wavelengths do not change much over time as a result of accurate temperature control, however, it is effective to use this color correction apparatus 51 to adjust the wavelength variation for example at the time that the product is shipped.

The color correction apparatus 51 includes a spectrum detector 53, a color correction signal acquisition unit 54, a calculator 55 of a signal for output calculation, an output calculator 56, and a memory 57. The light source apparatus 52 is configured to include a light source unit 58, a light source controller 59, and a laser-specific input signal memory 60. The light source unit 58 includes lasers $L_1$ to $L_6$ and a combiner 62 as in Embodiment 1. The output of each laser passes through an optical fiber 61, is combined by the combiner 62, and is then output to the optical fiber 63. The light source apparatus 52 is, for example, a light source for an endoscope and can be connected detachably to a non-illustrated endoscope by a connector 64.

Like the color imaging unit 32 in Embodiment 1, the spectrum detector 53 is a detector provided with a light receiving device that has wavelength sensitivity characteristics of three colors, red, green, and blue. The output of this detector is output to the color correction signal acquisition unit 54 and is further transmitted to the calculator 55 of the signal for output calculation.

The calculator 55 of the signal for output calculation, the output calculator 56, and the memory 57 in FIG. 15 are components with nearly identical functions to those of the calculator 24 of the imaging signal for output calculation, the output calculator 25, and the memory 26 in Embodiment 1. The light source unit 58, the light source controller 59, and the laser-specific input signal memory 60 are components with nearly identical functions to those of the light source unit 21, the light source controller 28, and the laser-specific input signal memory 27 in Embodiment 1. Accordingly, a description of these components is omitted.

When performing color correction on light source apparatuses 52, for example when shipping light source apparatuses 52, color correction is performed on each light source apparatus 52 in order to suppress individual color variation in each apparatus. Such color variation is caused by variation in the wavelength of each laser incorporated into the light source apparatus 52. Color correction processing is performed with the color correction apparatus 51 connected to the light source apparatus 52 via the connector 64. The color correction processing can be performed by the same method as in Embodiment 1 and Embodiment 2.

To implement the spectrum detector 53, the peak wavelength of each laser may be acquired by a direct spectrum analyzer or the like. By measuring the peak wavelength directly, an appropriate output ratio for the appropriate signal value of the laser group belonging to the narrow band light source group can be determined more easily and accurately. The color correction signal acquisition unit 54, calculator 55 of the signal for output calculation, output calculator 56, and memory 57 may, for example, be implemented on the same computer.

The appropriate output ratio that allows output of a color close to the appropriate signal value for the narrow band light source group is calculated and confirmed. This output ratio is then stored in the laser-specific input signal memory 60. In the case of color correction at the time the product is shipped, the product is shipped with the output ratio corrected. When the light source apparatus 52 is actually used, the user performs white balance correction, at a time such as before observation, on the basis of the output ratio stored in the laser-specific input signal memory 60.

In this way, according to this embodiment, correction for wavelength variation is completed at the time of product shipping, thereby reducing the burden on the user and allowing a stable image to be obtained. By using the same appropriate signal value in common for all products, the illumination color can be corrected to have little variation across products. Furthermore, since wavelength variation is corrected by a dedicated apparatus at the time of shipping, color correction can be performed more accurately. As in Embodiment 3, the color correction apparatus 51 can also be applied to an endoscopic apparatus for regular light observation and special light observation.

Embodiment 5

Figure 16:
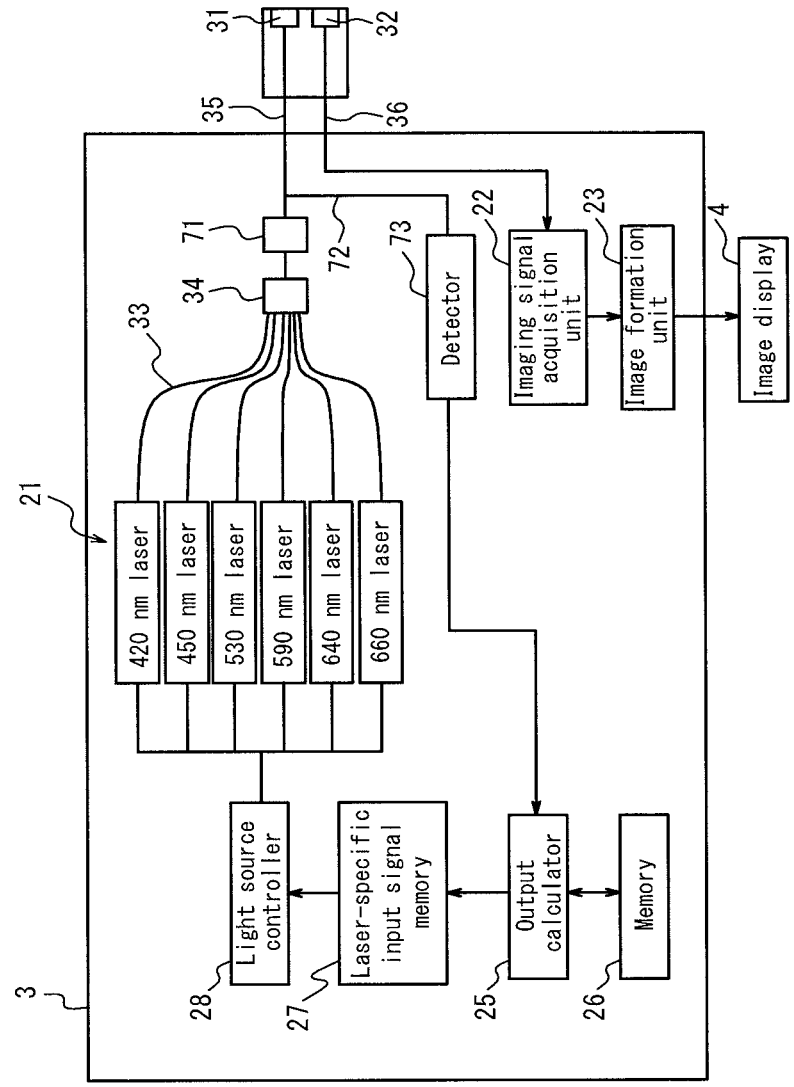
FIG. 16 is a block diagram of the main portion of an endoscopic system according to Embodiment 5.

FIG. 16 is a block diagram of the main portion of an endoscopic system according to Embodiment 5. This embodiment differs from the endoscopic system 1 in Embodiment 1 in that instead of the imaging unit being disposed at the tip of the insertion portion, illumination light emitted from the light source unit 21 is branched, and a separately provided detector 73 receives a branched portion of the illumination light. The illumination color is then corrected without use of the imaging unit or a standard subject. Therefore, the endoscopic system according to this embodiment includes a coupler 71 that branches a portion of the illumination light, an optical fiber 72 that guides the branched portion of the illumination light branched by the coupler, and a detector 73 that detects the illumination color from the portion of the illumination light guided by the optical fiber. The endoscopic system is configured so that output of the detector 73 is transmitted to the output calculator 25.

Figure 17:
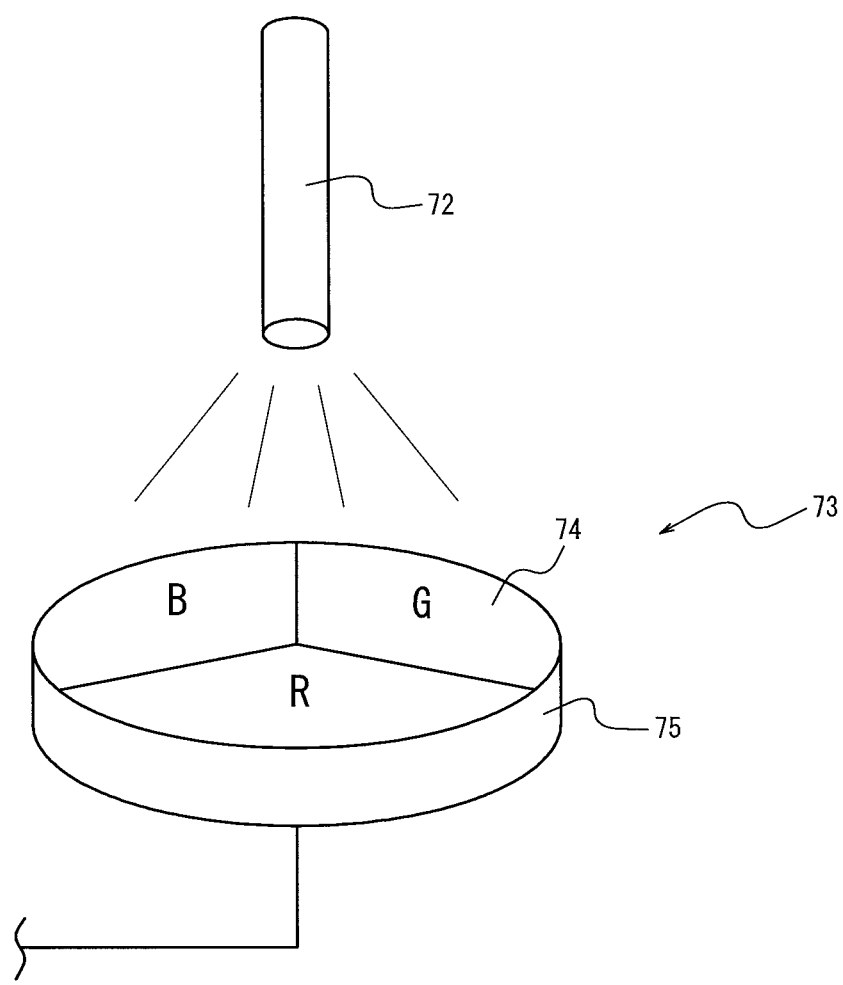
FIG. 17 illustrates the detector in FIG. 16.

FIG. 17 schematically illustrates the detector 73 and the optical fiber 72 connected to the detector 73. The detector 73 is a photodiode (PD) 75 with a color filter 74 disposed on the front surface thereof. The detector 73 has a function to convert the current illumination color to an RGB signal and transmit the RGB signal to the output calculator 25. Since the remaining configuration is similar to that of Embodiments 1 and 2, identical or corresponding components are labeled with the same reference signs, and a description thereof is omitted.

With this configuration, when the user begins observation using this endoscopic system, the detector 73 detects the illumination color of the illumination light from a portion of the illumination light and transmits the illumination color to the output calculator 25. On the basis of the acquired illumination color of the illumination light, as in Embodiments 1 and 2 the output calculator 25 optimizes the illumination color by performing correction in two stages. First, the output calculator 25 adjusts the illumination color of each narrow band light source group so as to approach the first appropriate illumination color. The output calculator 25 then performs correction so that the illumination color when causing the narrow band light sources of all of the narrow band light source groups to emit light becomes substantially identical to the second appropriate illumination color.

When performing observation using this endoscopic system, the user can perform the aforementioned two-stage correction before actually displaying an image on the image display. The user can also start the aforementioned correction intermittently after a certain time has passed during observation using this endoscopic system.

In this way, according to this embodiment, the illumination color can be corrected without the user manually placing and removing the standard subject. Furthermore, the illumination color can be corrected automatically. Hence, the burden on the user is reduced, and a stable image can always be obtained. As in Embodiment 3, this endoscopic system can also be applied to an endoscopic apparatus for regular light observation and special light observation.

This disclosure is not limited to the above embodiments, and a variety of changes and modifications may be made. For example, the wavelength and number of lasers and LEDs, the number of lasers and LEDs for each narrow band light source, and the way of grouping lasers and LEDs in each embodiment are only examples. A variety of other configurations may be adopted. The narrow band light source groups may also be configured with only LEDs, without including any lasers. For example, the type one narrow band light source group may be configured with only a plurality of LEDs, and output may be adjusted between LEDs.

The invention claimed is:

1. An endoscopic system comprising:
    an illumination apparatus configured to emit illumination light; and
    an image sensor configured to convert returning light returned from an observed part to an image signal, the returning light being produced by the illumination light emitted from the illumination apparatus,
    wherein the illumination apparatus comprises:
        a light source unit comprising a plurality of narrow band light sources, each with different peak wavelengths, the plurality of narrow band light sources being divided by peak wavelength into a plurality of narrow band light source groups, and each narrow band light source group that comprises a plurality of the narrow band light sources being designated as a type one narrow band light source group;
        a memory configured to store a first target signal output value having a plurality of wavelength components corresponding to a target illumination color for each type one narrow band light source group; and
        a controller configured to:
            for each type one narrow band light source group, perform a comparison of the first target signal output value of the type one narrow band light source group with a signal output value of the image signal detected by the image sensor upon the plurality of narrow band light sources belonging to the type one narrow band light source group emitting light and calculate a target output intensity for each narrow band light source belonging to the type one narrow band light source group on a basis of a result of the comparison; and
            control the plurality of narrow band light sources of the light source unit on a basis of the target output intensity calculated.

2. The endoscopic system of claim 1,
    wherein for each type one narrow band light source group, the controller is configured to calculate the target output intensity of each narrow band light source belonging to the type one narrow band light source group so that the signal output value detected by the image sensor approaches the first target signal output value of the type one narrow band light source group.

3. The endoscopic system of claim 1,
    wherein with a standard subject disposed at the observed part, the image sensor is configured to detect an image signal of the standard subject as the signal output value of the type one narrow band light source group, the image signal being acquired for each type one narrow band light source group.

4. The endoscopic system of claim 3,
    wherein the image sensor comprises a plurality of color light receiving elements having different wavelength sensitivity characteristics, and
    wherein a plurality of narrow band light sources belonging to a same type one narrow band light source group have peak wavelengths in a same wavelength region among a plurality of non-overlapping wavelength regions.

5. The endoscopic system of claim 4,
    wherein at least one type one narrow band light source group includes a narrow band light source used during special light observation.

6. The endoscopic system of claim 4,
    wherein at least a portion of a surface of the standard subject facing the image sensor has a white region.

7. The endoscopic system of claim 4,
    wherein N≥L and N≥M,
    where L, M, and N are natural numbers equal to or greater than one, L is a number of the narrow band light source groups, M is a maximum number of narrow band light sources belonging to any of the narrow band light source groups, and N is a number of types of colors of the color light receiving elements.

8. The endoscopic system of claim 7,
    wherein a number of the narrow band light sources included in the illumination apparatus is at least four and no greater than nine.

9. The endoscopic system of claim 3,
    wherein the image sensor comprises a plurality of color light receiving elements having different wavelength sensitivity characteristics, and
    wherein a plurality of narrow band light sources belonging to a same type one narrow band light source group have peak wavelengths in a plurality of different, non-overlapping wavelength regions.

10. The endoscopic system of claim 3,
    wherein the light source unit simultaneously emits light from the narrow band light sources belonging to the narrow band light source groups sequentially by narrow band light source group, and the image sensor acquires the image signal in conjunction with a timing of light emission of the narrow band light sources and generates a color image on a basis of the image signal, and
    wherein a portion of a surface of the standard subject facing the image sensor is divided into regions having three or more different colors.

11. The endoscopic system of claim 1,
    wherein the illumination light emitted from the illumination apparatus upon causing the narrow band light sources belonging to the plurality of narrow band light source groups to emit light is designated as observation illumination light, wherein the memory is configured to store a second target signal output value having a plurality of wavelength components, and wherein after calculating the target output intensity for each of the plurality of narrow band light sources in each type one narrow band light source group, the controller is configured to calculate output of each narrow band light source belonging to each of the plurality of narrow band light source groups, while maintaining an output ratio of the target output intensity of each narrow band light source belonging to a same type one narrow band light source group, so that a signal output value of the image signal obtained from the image sensor by emitting the observation illumination light approaches the second target signal output value.

12. The endoscopic system of claim 11,
wherein the second target signal output value is obtained by combining the plurality of narrow band light source groups, and wherein the controller is configured to calculate output of each narrow band light source belonging to the plurality of narrow band light source groups so that the observation illumination light has a signal output value substantially identical to the second target signal output value.

13. The endoscopic system of claim 1,
wherein the light source unit is configured to simultaneously emit light from the narrow band light sources belonging to the narrow band light source groups sequentially by narrow band light source group, and wherein the image sensor is configured to acquire the image signal in conjunction with a timing of light emission of the narrow band light sources and generate a color image on a basis of the image signal.

* * * * *